United States Patent
Itagaki

(10) Patent No.: US 7,253,301 B2
(45) Date of Patent: Aug. 7, 2007

(54) OPTICALLY ACTIVE COPPER CATALYST COMPOSITION

(75) Inventor: Makoto Itagaki, Katano (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 78 days.

(21) Appl. No.: 10/549,939

(22) PCT Filed: Mar. 25, 2004

(86) PCT No.: PCT/JP2004/004185

§ 371 (c)(1), (2), (4) Date: Sep. 20, 2005

(87) PCT Pub. No.: WO2004/087317

PCT Pub. Date: Oct. 14, 2004

(65) Prior Publication Data

US 2006/0211879 A1   Sep. 21, 2006

(30) Foreign Application Priority Data

Mar. 31, 2003 (JP) ............................. 2003-093750

(51) Int. Cl.
C07C 69/74 (2006.01)
C07C 213/00 (2006.01)

(52) U.S. Cl. ...................... 560/124; 564/287

(58) Field of Classification Search ........ 564/248, 564/282, 285, 287; 568/715, 716, 763; 560/102, 560/124, 116, 118; 562/506
See application file for complete search history.

(56) References Cited

U.S. PATENT DOCUMENTS 6,469,198 B2 * 10/2002 Suzukamo et al. ......... 560/124
2001/0037036 A1  11/2001 Suzukamo et al.
2002/0177718 A1  11/2002 Yamamoto et al.

FOREIGN PATENT DOCUMENTS

JP  2001-278851 A  10/2001
JP  2003-12675 A  1/2003

* cited by examiner

*Primary Examiner*—Karl Puttlitz
(74) *Attorney, Agent, or Firm*—Birch, Stewart, Kolasch & Birch, LLP

(57) ABSTRACT

There is provided an optically active copper catalyst composition comprising
(a) an optically active salicylideneaminoalcohol represented by the formula (1):

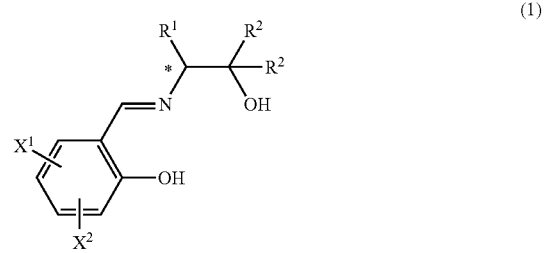

wherein $R^1$ and $R^2$ are the same or different, and independently represent a substituted or unsubstituted lower alkyl group, a substituted or unsubstituted aralkyl group, or a substituted or unsubstituted aryl group; $X^1$ and $X^2$ are the same or different, and independently represent a hydrogen atom, a lower alkoxy group, a nitro group, a lower alkoxycarbonyl group, a cyano group or a halogen atom; and * represents an asymmetric center, provided that both of $X^1$ and $X^2$ don't represent hydrogen atoms,
(b) a monovalent or divalent copper compound, and
(c-1) a lithium compound or
(c-2) a compound selected from aluminum compounds having Lewis acidity, titanium compounds having Lewis acidity, boron compounds having Lewis acidity, zirconium compounds having Lewis acidity and hafnium compounds having Lewis acidity; and a process for producing an optically active cyclopropane compound by using the same.

13 Claims, No Drawings

OPTICALLY ACTIVE COPPER CATALYST COMPOSITION

This application is filed under 35 USC 371, and claims the benefit of PCT/JP04/04185, filed Mar. 25, 2004.

TECHNICAL FIELD

The present invention relates to a novel optically active copper catalyst composition and process for production of a cyclopropane compound using the same.

BACKGROUND ART

Optically active cyclopropane compounds are important compounds as synthesis intermediates of pharmaceuticals and/or agricultural chemicals. For example, (+)-2,2-dimethyl-3-(2-methyl-1-propenyl)cyclopropanecarboxylic acid, which is a representative optically active cyclopropane compound, has been known to be useful for an acidic moiety of a synthesized pyrethroid type insecticide. As a method for producing the optically active cyclopropane compounds, for example, method for reacting 2,5-dimethyl-2,4-hexadiene with a diazoacetic acid ester in the presence of an optically active salicylideneaminoalcohol copper complex catalyst is known (e.g. JP 59-225194 A), and improving the catalyst activity by modifying the substituents of salicylideneaminoalcohol has been tried (e.g. JP 2001-278853 A).

DISCLOSURE OF THE INVENTION

According to the present invention, a diazotization reaction catalyst which exhibits good activity is obtained, and an optically active cyclopropane compound can be produced easily by using the catalyst.

That is, the present invention provides, 1. an optically active copper catalyst composition (hereinafter, simply preferred to as the copper catalyst composition of the present invention) comprising
   (a) an optically active salicylideneaminoalcohol represented by the formula (1):

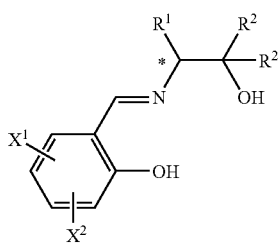

(1)

wherein $R^1$ and $R^2$ are the same or different, and independently represent a substituted or unsubstituted lower alkyl group, a substituted or unsubstituted aralkyl group, or a substituted or unsubstituted aryl group;

$X^1$ and $X^2$ are the same or different, and independently represent a hydrogen atom, a lower alkoxy group, a nitro group, a lower alkoxycarbonyl group, a cyano group or a halogen atom; and * represents an asymmetric center, provided that both of $X^1$ and $X^2$ don't represent hydrogen atoms (hereinafter, simply preferred to as the optically active salicylideneaminoalcohol (1)), (b) a monovalent or divalent copper compound, and (c-1) a lithium compound or (c-2) a compound selected from aluminum compounds having Lewis acidity, titanium compounds having Lewis acidity, boron compounds having Lewis acidity, zirconium compounds having Lewis acidity and hafnium compounds having Lewis acidity; and 2. A process for producing an optically active cyclopropane compound represented by the formula (4):

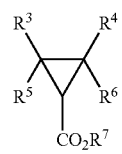

(4)

wherein $R^3$, $R^4$, $R^5$ and $R^6$ are the same or different, and independently represent a hydrogen atom, an alkyl group which may be substituted with one or more halogen atom, an alkenyl group which may be substituted with one or more halogen atom, an aryl group or an aralkyl group; provided that, when $R^3$ and $R^5$ are the same, $R^3$ and $R^4$ are different from each other; and $R^7$ represents a C1-6 alkyl group (hereinafter, simply preferred to as the optically active cyclopropane compound (4)), which comprises reacting a prochiral olefin represented by the formula (2):

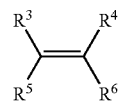

(2)

wherein $R^3$, $R^4$, $R^5$ and $R^6$ are as defined above (hereinafter, simply preferred to as the olefin (2)), with a diazoacetic acid ester represented by the formula (3):

$$N_2CHCO_2R^7 \quad (3)$$

wherein $R^7$ is as described above (hereinafter, simply preferred to as the diazoacetic acid ester (3)), in the presence of the above-mentioned optically active copper catalyst composition.

BEST MODE FOR CARRYING OUT THE PRESENT INVENTION

The copper catalyst composition of the present invention will be illustrated below.

In the optically active salicylideneaminoalcohol (1), the unsubstituted lower alkyl group represented by $R^1$ or $R^2$ include, for example, a C1–4 alkyl group such as a methyl, ethyl, n-propyl, isopropyl, n-butyl, isobutyl and tert-butyl group. Examples of the substituent of the substituted lower alkyl group include, for example, a C1-4 lower alkoxy group such as a methoxy, ethoxy, propoxy and butoxy group.

Examples of the unsubstituted aryl group include, for example, a phenyl group. Examples of the substituent of the substituted aryl group include, for example, a substituent selected from a lower alkyl group (for example, C1–4 alkyl group like the above), a lower alkoxy group (for example, C1–4 alkoxy group like the above) and the like.

Specific examples of the substituted aryl group include, for example, a 2-methoxyphenyl and a 2-n-butoxy-5-tert-butylphenyl group.

Examples of the unsubstituted aralkyl group include, for example, lower alkyl groups substituted with a unsubstituted aryl group (for example, a phenyl group), and examples of the substituted aralkyl group include lower alkyl groups substituted with the substituted aryl group like the above (for example, an aryl group substituted with a C1–4 alkyl group or a C1–4 alkoxy group). Examples of the lower alkyl group of the lower alkyl group substituted with the unsubstituted or substituted aryl group include, for example, a C1–4 alkyl group like the above. Specific examples of them include, for example, a benzyl and 2-methoxybenzyl group.

$X^1$ and $X^2$ in the formula of the above-mentioned optically active salicylidenaminoalcohol (1) will be illustrated below.

Examples of the lower alkoxy group represented by $X^1$ and $X^2$ include, for example, a lower alkoxy group having 1 to 4 carbon atoms such as a methoxy, ethoxy, propoxy and butoxy group.

Examples of the lower alkoxy group of the lower alkoxycarbonyl group represented by $X^1$ and $X^2$ include the above-mentioned C1–4 alkoxy group, and specific examples of the lower alkoxycarbonyl group include, for example, a methoxycarbonyl, ethoxycarbonyl, propoxycarboyl and butoxycarbonyl group.

Examples of the halogen atom represented by $X^1$ and $X^2$ include, for example, a fluorine, chlorine and bromine atom.

Examples of the optically active salicylideneaminoalcohol (1) include, for example, (R)-N-(3-nitrosalicylidene)-2-amino-1,1-diphenyl-1-propanol, (R)-N-(5-nitrosalicylidene)-2-amino-1,1-diphenyl-1-propanol, (R)-N-(3,5-dinitrosalicylidene)-2-amino-1,1-diphenyl-1-propanol, (R)-N-(3-chlorosalicylidene)-2-amino-1,1-diphenyl-1-propanol, (R)-N-(5-chlorosalicylidene)-2-amino-1,1-diphenyl-1-propanol, (R)-N-(3,5-dichlorosalicylidene)-2-amino-1,1-diphenyl-1-propanol, (R)-N-(3-fluorosalicylidene)-2-amino-1,1-diphenyl-1-propanol, (R)-N-(5-fluorosalicylidene)-2-amino-1,1-diphenyl-1-propanol, (R)-N-(3-bromosalicylidene)-2-amino-1,1-diphenyl-1-propanol, (R)-N-(5-bromosalicylidene)-2-amino-1,1-diphenyl-1-propanol, (R)-N-(3-methoxycarbonylsalicylidene)-2-amino-1,1-diphenyl-1-propanol, (R)-N-(5-methoxycarbonylsalicylidene)-2-amino-1,1-diphenyl-1-propanol, (R)-N-(3-cyanosalicylidene)-2-amino-1,1-diphenyl-1-propanol, (R)-N-(5-cyanosalicylidene)-2-amino-1,1-diphenyl-1-propanol, (R)-N-(3-fluoro-5-nitrosalicylidene)-2-amino-1,1-diphenyl-1-propanol, (R)-N-(3-methoxysalicylidene)-2-amino-1,1-diphenyl-1-propanol, (R)-N-(5-methoxysalicylidene)-2-amino-1,1-diphenyl-1-propanol, (R)-N-(3-nitrosalicylidene)-2-amino-1,1-di(2-methoxyphenyl)-1-propanol, (R)-N-(5-nitrosalicylidene)-2-amino-1,1-di(2-methoxyphenyl)-1-propanol, (R)-N-(3,5-dinitrosalicylidene)-2-amino-1,1-di(2-methoxyphenyl)-1-propanol, (R)-N-(3-chlorosalicylidene)-2-amino-1,1-di(2-methoxyphenyl)-1-propanol, (R)-N-(5-chlorosalicylidene)-2-amino-1,1-di(2-methoxyphenyl)-1-propanol, (R)-N-(3,5-dichlorosalicylidene)-2-amino-1,1-di(2-methoxyphenyl)-1-propanol, (R)-N-(3-fluorosalicylidene)-2-amino-1,1-di(2-methoxyphenyl)-1-propanol, (R)-N-(5-fluorosalicylidene)-2-amino-1,1-di(2-methoxyphenyl)-1-propanol, (R)-N-(3-bromosalicylidene)-2-amino-1,1-di(2-methoxyphenyl)-1-propanol, (R)-N-(5-bromosalicylidene)-2-amino-1,1-di(2-methoxyphenyl)-1-propanol, (R)-N-(3-methoxycarbonylsalicylidene)-2-amino-1,1-di(2-methoxyphenyl)-1-propanol, (R)-N-(5-methoxycarbonylsalicylidene)-2-amino-1,1-di(2-methoxyphenyl)-1-propanol, (R)-N-(3-cyanosalicylidene)-2-amino-1,1-di(2-methoxyphenyl)-1-propanol, (R)-N-(5-cyanosalicylidene)-2-amino-1,1-di(2-methoxyphenyl)-1-propanol, (R)-N-(3-fluoro-5-nitrosalicylidene)-2-amino-1,1-di(2-methoxyphenyl)-1-propanol, (R)-N-(3-methoxysalicylidene)-2-amino-1,1-di(2-methoxyphenyl)-1-propanol, (R)-N-(5-methoxysalicylidene)-2-amino-1,1-di(2-methoxyphenyl)-1-propanol, (R)-N-(3-nitrosalicylidene)-2-amino-1,1-di(5-tert-butyl-2-n-butoxyphenyl)-1-propanol, (R)-N-(5-nitrosalicylidene)-2-amino-1,1-di(5-tert-butyl-2-n-butoxyphenyl)-1-propanol, (R)-N-(3,5-dinitrosalicylidene)-2-amino-1,1-di(5-tert-butyl-2-n-butoxyphenyl)-1-propanol, (R)-N-(3-chlorosalicylidene)-2-amino-1,1-di(5-tert-butyl-2-n-butoxyphenyl)-1-propanol, (R)-N-(5-chlorosalicylidene)-2-amino-1,1-di(5-tert-butyl-2-n-butoxyphenyl)-1-propanol, (R)-N-(3,5-dichlorosalicylidene)-2-amino-1,1-di(5-tert-butyl-2-n-butoxyphenyl)-1-propanol, (R)-N-(3-fluorosalicylidene)-2-amino-1,1-di(5-tert-butyl-2-n-butoxyphenyl)-1-propanol, (R)-N-(5-fluorosalicylidene)-2-amino-1,1-di(5-tert-butyl-2-n-butoxyphenyl)-1-propanol, (R)-N-(3-bromosalicylidene)-2-amino-1,1-di(5-tert-butyl-2-n-butoxyphenyl)-1-propanol, (R)-N-(5-bromosalicylidene)-2-amino-1,1-di(5-tert-butyl-2-n-butoxyphenyl)-1-propanol, (R)-N-(3-methoxycarbonylsalicylidene)-2-amino-1,1-di(5-tert-butyl-2-n-butoxyphenyl)-1-propanol, (R)-N-(5-methoxycarbonylsalicylidene)-2-amino-1,1-di(5-tert-butyl-2-n-butoxyphenyl)-1-propanol, (R)-N-(3-cyanosalicylidene)-2-amino-1,1-di(5-tert-butyl-2-n-butoxyphenyl)-1-propanol, (R)-N-(5-cyanosalicylidene)-2-amino-1,1-di(5-tert-butyl-2-n-butoxyphenyl)-1-propanol, (R)-N-(3-fluoro-5-nitrosalicylidene)-2-amino-1,1-di(5-tert-butyl-2-n-butoxyphenyl)-1-propanol, (R)-N-(3-methoxysalicylidene)-2-amino-1,1-di(5-tert-butyl-2-n-butoxyphenyl)-1-propanol, (R)-N-(5-methoxysalicylidene)-2-amino-1,1-di(5-tert-butyl-2-n-butoxyphenyl)-1-propanol, (R)-N-(3-nitrosalicylidene)-2-amino-1,1-di(5-tert-butyl-2-n-butoxyphenyl)-3-phenyl-1-propanol, (R)-N-(5-nitrosalicylidene)-2-amino-1,1-di(5-tert-butyl-2-n-butoxyphenyl)-3-phenyl-1-propanol, (R)-N-(3,5-dinitrosalicylidene)-2-amino-1,1-di(5-tert-butyl-2-n-butoxyphenyl)-3-phenyl-1-propanol, (R)-N-(3-chlorosalicylidene)-2-amino-1,1-di(5-tert-butyl-2-n-butoxyphenyl)-3-phenyl-1-propanol, (R)-N-(5-chlorosalicylidene)-2-amino-1,1-di(5-tert-butyl-2-n-butoxyphenyl)-3-phenyl-1-propanol, (R)-N-(3,5-dichlorosalicylidene)-2-amino-1,1-di(5-tert-butyl-2-n-butoxyphenyl)-3-phenyl-1-propanol, (R)-N-(3-fluorosalicylidene)-2-amino-1,1-di(5-tert-butyl-2-n-butoxyphenyl)-3-phenyl-1-propanol, (R)-N-(5-fluorosalicylidene)-2-amino-1,1-di(5-tert-butyl-2-n-butoxyphenyl)-3-phenyl-1-propanol, (R)-N-(3-bromosalicylidene)-2-amino-1,1-di(5-tert-butyl-2-n-butoxyphenyl)-3-phenyl-1-propanol, (R)-N-(5-bromosalicylidene)-2-amino-1,1-di(5-tert-butyl-2-n-butoxyphenyl)-3-phenyl-1-propanol, (R)-N-(3-methoxycarbonylsalicylidene)-2-amino-1,1-di(5-tert-butyl-2-n-butoxyphenyl)-3-phenyl-1-propanol, (R)-N-(5-methoxycarbonylsalicylidene)-2-amino-1,1-di(5-tert-butyl-2-n-butoxyphenyl)-3-phenyl-1-propanol, (R)-N-(3-cyanosalicylidene)-2-amino-1,1-di(5-tert-butyl-2-n-butoxyphenyl)-3-phenyl-1-propanol, (R)-N-(5-cyanosalicylidene)-2-amino-1,1-di(5-tert-butyl-2-n-butoxyphenyl)-3-phenyl-1-propanol, (R)-N-(3-fluoro-5-nitrosalicylidene)-2-amino-1,1-di(5-tert-butyl-2-n-butoxyphenyl)-3-phenyl-1-propanol, (R)-N-(3-methoxysalicylidene)-2-amino-1,1-di(5-tert-butyl-2-n-butoxyphenyl)-3-phenyl-1-propanol, (R)-N-(5-methoxysalicylidene)-2-amino-1,1-di(5-tert-butyl-2-n- butoxyphenyl)-3-phenyl-1-propanol, and these compounds in which the configuration (R) is changed to (S).

The optically active salicylideneaminoalcohol has R- and S-isomer, and in the present invention, either any one of the isomers may be used.

The optically active salicylideneaminoalcohol (1) can be produced according to a method of reaction of a corresponding aminoalcohol and a corresponding salicylaldehyde (described in e.g. JP-2001-278853 A and the corresponding U.S. patent application Numbers 2001037036 and 2002004618, U.S. Pat. Nos. 6,469,198 and 6,670,500).

Examples of the monovalent or divalent copper compound include, for example, a C2–15 copper organic carboxylate such as copper(I) acetate, copper (II) acetate, copper(II) naphthenate and copper(II) octanoate, and a monovalent or divalent copper salt or copper complex such as copper(II) acetylacetonate, copper(I) chloride, copper(II) chloride, copper(I) bromide, copper(II) bromide, copper(II) methanesulfonate, copper(I) trifluoromethanesulfonate, copper(II) trifluoromethanesulfonate, copper(II) carbonate and copper(II) hydroxide. The copper compound may be used alone or two or more thereof may be combined to use.

Examples of the lithium compound include, for example, a lithium salt represented by lithium halide such as lithium chloride, lithium bromide, lithium iodide and lithium fluoride, alkoxylithium such as methoxylithium, ethoxylithium, propoxylithium and butoxylithium, lithium hydroxide or a mixture thereof.

Aluminum compounds having Lewis acidity, titanium compounds having Lewis acidity, boron compounds having Lewis acidity, zirconium compounds having Lewis acidity and hafnium compounds having Lewis acidity will be illustrated below.

Examples of aluminum compounds having Lewis acidity include, for example, trihaloaluminum such as aluminum trichloride, trialkylaluminum such as trimethylaluminum, triethylaluminum and triisobutylaluminum, trialkoxyaluminum such as triethoxyaluminum, triaryloxyaluminum such as triphenoxyaluminum, and tris(pentafluorophenyl)aluminum.

Examples of titanium compounds having Lewis acidity include, for example, tetrahalotitanium such as titanium tetrachloride, and tetraalkoxytitanium such as tetraisopropoxytitanium and tetra(n-butoxy)titanium.

Examples of boron compounds having Lewis acidity include, for example, boron trifluoride diethyl etherate, triethylborane, triphenylborane, and tris(pentafluorophenyl)borane.

Examples of zirconium compounds having Lewis acidity include, for example, zirconium halide (IV) or the complex such as zirconium tetrachloride and zirconium tetrachloride tetrahydrofuran complex, and tetraalkoxyzirconium such as tetra(n-butoxy)zirconium.

Examples of hafnium compounds having Lewis acidity include, for example, hafnium halide (IV) or the complex such as hafnium tetrachloride and hafnium tetrachloride tetrahydrofuran complex.

Triethoxylaluminum, tris(pentafluorophenyl)aluminum, tetraisopropoxytitanium, and tris(pentafluorophenyl)borane are preferable. The compound having Lewis acidity may be used alone or two or more thereof may be combined to use.

The optically active copper catalyst composition of the present invention is produced by contacting the optically active salicylideneaminoalcohol (1), the monovalent or divalent copper compound and the above-mentioned c-1) the lithium compound or the above-mentioned compound selected from c-2) usually in an organic solvent. The amount of the optically active salicylideneaminoalcohol (1) used is usually about 0.5 to 2 moles per 1 mole of the monovalent or divalent copper compound and the amount of the above-mentioned c-1) the lithium compound or the above-mentioned compound selected from c-2) used is usually about 0.3 to 5 moles per 1 mole of the monovalent or divalent copper compound.

The solvent may be a solvent which can dissolved a certain amount of the optically active copper complex of the present invention, and examples of the solvent include, for example, aromatic hydrocarbon solvents such as toluene and xylene; aliphatic hydrocarbon solvents such as hexane, cyclohexane and heptane; halogenated hydrocarbon solvents such as chloroform, dichloroethane and chlorobutane; and ester solvents such as ethyl acetate and ethyl propionate. The solvent may be used alone or in the form of a mixture.

The temperature of contacting the optically active salicylideneaminoalcohol (1), the monovalent or divalent copper compound and the above-mentioned c-1) the lithium compound or the above-mentioned compound selected from c-2) is usually 0° C. to boiling point of the solvent.

Contacting the optically active salicylideneaminoalcohol (1), the monovalent or divalent copper compound and the above-mentioned c-1) the lithium compound or the above-mentioned compound selected from c-2) may be carried out by mixing three components in the organic solvent, and the mixing order is not particularly limited. After isolating the complex obtained by contacting the optically active salicylideneaminoalcohol (1) and the monovalent or divalent copper compound, the complex may be contacted the above-mentioned c-1) the lithium compound or the above-mentioned compound selected from c-2). Contacting the optically active salicylideneaminoalcohol (1) and the monovalent or divalent copper compound may be carried out in the presence of a base such as sodium methylate.

A solution or slurry containing the optically active copper catalyst composition is usually obtained by contacting the optically active salicylideneaminoalcohol (1), the monovalent or divalent copper compound and the Lewis acid in the organic solvent, and the optically active copper catalyst composition can be isolated by concentrating or filtering the solution or slurry. The solution or slurry containing the optically active copper catalyst composition may be used as it is for the cyclopropanation reaction described below.

Next, the following description will illustrate the process for producing an optically active cyclopropane compound represented by the formula (4) (hereinafter, simply preferred to as the optically active cyclopropane compound (4)), which comprises reacting the prochiral olefin represented by the formula (2) (hereinafter, simply preferred to as the olefin (2)) with the diazoacetic acid ester represented by the formula (3) (hereinafter, simply preferred to as the diazoacetic acid ester (3)) in the presence of the optically active copper catalyst composition obtained above.

In the formula of the above-mentioned olefin (2), examples of the alkyl group which may be substituted with one or more halogen atoms include, for example, C1–6 alkyl group such as a methyl, ethyl, n-propyl, isopropyl, n-butyl, isobutyl, n-pentyl, and hexyl group, and these alkyl groups whose one or more hydrogen atoms are substituted with the above-mentioned halogen atoms such as a chloromethyl, fluoromethyl, trifluoromethyl, and chloroethyl group. Examples of the alkenyl group which may be substituted with one or more halogen atoms include a C2–6 alkenyl group such as a vinyl, 1-propenyl, 2-propenyl, 2-methyl-1-propenyl, 1-butenyl, 2-butenyl and 3-butenyl group, and these alkenyl groups whose one or more hydrogen atoms are substituted with the above-mentioned halogen atoms such as a 1-chloro-2-propenyl group. As the aryl and aralkyl group, there are, for example, the same groups as R1 and R2 exemplified above.

Examples of the olefin (2) include, for example, propene, 1-butene, isobutylene, 1-pentene, 1-hexene, 1-octene, 4-chloro-1-butene, 2-pentene, 2-heptene, 2-methyl-2-butene, 2,5-dimethyl-2,4-hexadiene, 2-chloro-5-methyl-2,4-hexadiene, 2-fluoro-5-methyl-2,4-hexadiene, 1,1,1-trifluoro-5-methyl-2,4-hexadiene, 2-methoxycarbonyl-5-methyl-2,4-hexadiene, 1,1-difluoro-4-methyl-1,3-pentadiene, 1,1-dichloro-4-methyl-1,3-pentadiene, 1,1-dibromo-4-methyl-1,3-pentadiene, 1-chioro-1-fluoro-4-methyl-1,3-pentadiene 1-fluoro-1-bromo-4-methyl-1,3-pentadiene, 2-methyl-2,4-hexadiene, 1-fluro-1,1-dichloro-4-methyl-2-pentene, 1,1,1-trichloro-4-methyl-3-pentene, 1,1,1-tribromo-4-methyl-3-pentene, 2,3-dimethyl-2-pentene, 2-methyl-3-phenyl-2-butene, 2-bromo-2,5-dimethyl-4-hexene 2-chloro-2,5-dimethyl-4-hexene, and 2,5-dimethyl-6-chloro-2,4-hexadiene.

Examples of C1–6 alkyl group in the formula of the above-mentioned diazoacetic acid ester (3) include, for example, a C1–6 alkyl group such as a methyl, ethyl, n-propyl, isopropyl, n-butyl, isobutyl, n-pentyl and hexyl group.

Examples of the diazoacetic acid ester (3) include, for example, methyl diazoacetate, ethyl diazoacetate, n-propyl diazoacetate, isopropyl diazoacetate, n-butyl diazoacetate, isobutyl diazoacetate and tert-butyl diazoacetate.

The amount of the olefin (2) to be used is usually 1 mole or more, preferably 1.2 moles or more relative to 1 mole of the diazoacetic acid ester (3). There is no specific upper limit and when the olefin (2) is a liquid, large excess thereof can be used also to serve as the solvent.

As the optically active copper complex composition, the either composition having ligand of (R)-isomer or (S)-isomer may be used as described above and a mixture thereof in which one of them exists in excess than the other may be used. The amount of the optically active copper complex to be used is usually about 0.0001 to 0.05 mole, preferably about 0.0005 to 0.01 mole in terms of the copper metal relative to 1 mole of the diazoacetic acid ester (3).

The reaction of the olefin (2) and the diazoacetic acid ester (3) is usually carried out by mixing three components, the optically active copper catalyst composition, the olefin (2), and the diazoacetic acid ester (3), in an atmosphere of an inert gas such as argon gas or nitrogen gas. The mixing order is not particularly limited. Usually, the diazoacetic acid ester (3) is added to a mixture of the optically active copper catalyst composition and the olefin (2). When the divalent copper compound is used for preparing the optically active copper catalyst composition, the reaction may be carried out in the presence of a reducing agent such as phenylhydrazine.

The reaction of the olefin (2) and diazoacetic acid ester (3) is usually carried out in the presence of a solvent. Examples of the solvent include, for example, halogenated hydrocarbon solvent such as dichloromethane, chloroform and carbon tetrachloride; aliphatic hydrocarbon solvent such as hexane, heptane and cyclohexane; aromatic hydrocarbon solvent such as benzene, toluene and xylene; and ester solvent such as ethyl acetate. The solvent can be used alone or in the form of a mixture. Although the amount of the solvent to be used is not particularly limited, in view of the volume efficiency and the properties of the reaction mixture, the amount of the solvent to be used is usually about 2 to 30 parts by weight, preferably 5 to 20 parts by weight relative to 1 part by weight of the diazoacetic acid ester (3). The solvent can be mixed previously with the olefin (2), the diazoacetic acid ester (3), and/or the optically active copper catalyst composition. Alternatively, as described above, when the olefin (2) is a liquid, the olefin (2) can also be used as the solvent.

Since the copper catalyst composition of the present invention has a superior catalytic activity at low temperature, the reaction can be carried out at lower reaction temperature than ever before. The reaction temperature is usually about −50 to 50° C., preferably −20 to 30° C.

After completion of the reaction, the optically active cyclopropane compound (4) can be isolated by, for example, concentrating the reaction mixture. The isolated optically active cyclopropane compound (4) can further be purified by a conventional purification means such as distillation, column chromatography, and the like.

Examples of the optically active cyclopropane compound (4) include, for example, optically active methyl 2-methylcyclopropanecarboxylate, optically active methyl 2,2-dimethylcyclopropanecarboxylate, optically active methyl 2,2-dimethyl-3-(2-methyl-1-propenyl)cyclopropanecarboxylate, optically active methyl 2,2-dimethyl-3-(2,2-dichloro-1-ethenyl)cyclopropanecarboxylate, optically active methyl 2,2-dimethyl-3-(2,2,2-trichloroethyl)cyclopropanecarboxylate, optically active methyl 2,2-dimethyl-3-(2,2,2-tribromoethyl)cyclopropanecarboxylate, optically active methyl 2,2-dimethyl-3-(2,2-dibromo-1-ethenyl)cyclopropanecarboxylate, optically active methyl 2,2-dimethyl-3-(2,2-difluoro-1-ethenyl)cyclopropanecarboxylate, optically active methyl 2,2-dimethyl-3-(2-fluoro-2-chloro-1-ethenyl)cyclopropanecarboxylate, optically active methyl 2,2-dimethyl-3-(2-fluoro-2-bromo-1-ethenyl)cyclopropanecarboxylate, optically active methyl 2,2-dimethyl-3-(2-fluoro-1-propenyl)cyclopropanecarboxylate, optically active methyl 2,2-dimethyl-3-(2-chloro-1-propenyl)cyclopropanecarboxylate, optically active methyl 2,2-dimethyl-3-(2-chloro-2,2,2-trifluoromethylethenyl)cyclopropanecarboxylate, optically active methyl 2,2-dimethyl-3-(2-methoxycarbonyl-1-propenyl)cyclopropanecarboxylate, optically active methyl 2,2-dimethyl-3-(2-chloro-2-methylpropyl)cyclopropanecarboxylate, optically active methyl 2,2-dimethyl-3-(2-bromo-2-methylpropyl)cyclopropanecarboxylate, and optically active methyl 2,2-dimethyl-3-(1-propenyl)cyclopropanecarboxylate; and compounds wherein the above methyl ester moieties are replaced with ethyl, n-propyl, isopropyl, isobutyl and tert-butyl ester moieties.

The optically active cyclopropane compound (4) can be converted into an optically active cyclopropanecarboxylic acid in which $R^7$ is a hydrogen atom by hydrolysis according to a known hydrolysis method.

EXAMPLES

The present invention will be further illustrated in more detail by Examples. The present invention is not limited to these Examples. The yield of the optically active cyclopropane compound, the trans-isomer/cis-isomer ratio and the residual ratio of diazoacetic acid ester were calculated from results of gas chromatography.

The optically purity of the optically active cyclopropane compound was calculated from results of liquid chromatography analysis. A trans-isomer means the compound having the ester group at 1-position and the 2-methyl-1-propenyl group at 3-position on the opposite side with respect to the cyclopropane ring plane and a cis-isomer means the compound having the ester group at 1-position and the 2-methyl- 1-propenyl group at 3-position on the same side with respect to the cyclopropane ring plane.

Example 1

To a 50 mL Schlenk tube purged with nitrogen, 8.73 mg of (R)-N-(5-nitrosalicylidene)-2-amino-1,1-di(2-methoxyphenyl)-1-propanol, 4.0 mg of copper (II) acetate monohydrate and 5 mL of ethyl acetate were added and mixed with stirring at an inner temperature of 50° C. for 30 minutes. 5.68 mg of tetraisopropoxytitanium was added to this solution. The resulting solution was stirred at room temperature for 10 minutes to effect reaction and the optically active copper catalyst composition was prepared. After adding 4 mg of phenylhydrazine to this solution containing the optically active copper catalyst composition, 7.8 g of 2,5-dimethyl-2,4-hexadiene was added thereto and the inner temperature was adjusted to 20° C. 5 mL of the ethyl acetate solution containing 1.14 g of ethyl diazoacetate was added dropwise thereto over 2 hours. After adding dropwise, the resulting mixture was stirred at the same temperature for 30 minutes to effect reaction and the reaction solution containing optically active ethyl 2,2-dimethyl-3-(2-methyl-1-propenyl)cyclopropanecarboxylate was obtained. The yield of optically active ethyl 2,2-dimethyl-3-(2-methyl-1-propenyl)cyclopropanecarboxylate was 85% (based on ethyl diazoacetate), the trans-isomer/cis-isomer ratio=58/42, and the residual ratio of ethyl diazoacetate was 0.1%. Also, optical purity of the trans-isomer was 76% e.e. and that of the cis-isomer was 70% e.e.

Comparative Example 1

According to the same manner as that described in Example 1, optically active ethyl 2,2-dimethyl-3-(2-methyl-1-propenyl)cyclopropanecarboxylate was obtained in a yield of 58% and the trans-isomer/cis-isomer ratio=58/42 except that tetraisopropoxytitanium was not used. The residual ratio of ethyl diazoacetate was 20%. Also, optical purity of the trans-isomer was 75% e.e. and that of the cis-isomer was 70% e.e.

Example 2

According to the same manner as that described in Example 1, optically active ethyl 2,2-dimethyl-3-(2-methyl-1-propenyl)cyclopropanecarboxylate was obtained in a yield of 61% and the trans-isomer/cis-isomer ratio=57/4.3 except that ethyl diazoacetate was added dropwise at 0° C. The residual ratio of ethyl diazoacetate was 3%. Optical purity of the trans-isomer was 84% e.e. and that of the cis-isomer was 78% e.e.

Comparative Example 2

According to the same manner as that described in Example 2, optically active ethyl 2,2-dimethyl-3-(2-methyl-1-propenyl)cyclopropanecarboxylate was obtained in a yield of 35% and the trans-isomer/cis-isomer ratio=57/43 except that tetraisopropoxytitanium was not used. The residual ratio of ethyl diazoacetate was 47%. Optical purity of the trans-isomer was 83% e.e. and that of the cis-isomer was 78% e.e.

Example 3

According to the same manner as that described in Example 1, optically active ethyl 2,2-dimethyl-3-(2-methyl-1-propenyl)cyclopropanecarboxylate was obtained in a yield of 92% and the trans-isomer/cis-isomer ratio=58/42 except that 3.57 mg of triethoxyaluminium was used in place of 5.68 mg of tetraisopropoxytitanium. The residual ratio of ethyl diazoacetate was 0.1%. Optical purity of the trans-isomer was 77% e.e. and that of the cis-isomer was 71% e.e.

Example 4

According to the same manner as that described in Example 3, optically active ethyl 2,2-dimethyl-3-(2-methyl-1-propenyl)cyclopropanecarboxylate was obtained in a yield of 70% and the trans-isomer/cis-isomer ratio=57/43 except that ethyl diazoacetate was added dropwise at 0° C. The residual ratio of ethyl diazoacetate was 5%. Optical purity of the trans-isomer was 84% e.e. and that of the cis-isomer was 78% e.e.

Example 5

According to the same manner as that described in Example 1, optically active ethyl 2,2-dimethyl-3-(2-methyl-1-propenyl)cyclopropanecarboxylate was obtained in a yield of 65% and the trans-isomer/cis-isomer ratio=58/42 except that 7.55 mg of zirconium tetrachloride tetrahydofuran complex was used in place of 5.68 mg of tetraisopropoxytitanium. The residual ratio of ethyl diazoacetate was 0.1%. Optical purity of the trans-isomer was 71% e.e. and that of the cis-isomer was 61% e.e.

Example 6

According to the same manner as that described in Example 1, optically active ethyl 2,2-dimethyl-3-(2-methyl-1-propenyl)cyclopropanecarboxylate was obtained in a yield of 84% and the trans-isomer/cis-isomer ratio=58/42 except that 9.29 mg of hafnium tetrachloride tetrahydofuran complex was used in place of 5.68 mg of tetraisopropoxytitanium. The residual ratio of ethyl diazoacetate was 0.1%. Optical purity of the trans-isomer was 76% e.e. and that of the cis-isomer was 71% e.e.

Example 7

According to the same manner as that described in Example 1, optically active ethyl 2,2-dimethyl-3-(2-methyl-1-propenyl)cyclopropanecarboxylate was obtained in a yield of 96% and the trans-isomer/cis-isomer ratio=58/42 except that 10.24 mg of tris(pentafluorophenyl)borane was used in place of 5.68 mg of tetraisopropoxytitanium. The residual ratio of ethyl diazoacetate was 0.1%. Optical purity of the trans-isomer was 77% e.e. and that of the cis-isomer was 71% e.e.

Reference Example 1

In a 200 mL flask, 87.3 mg of (R)-N-(5-nitrosalicylidene)-2-amino-1,1-di(2-methoxyphenyl)-1-propanol, 40 mg of copper(II) acetate monohydrate, and 50 mL of ethyl acetate were added and mixed with stirring at an inner temperature of 50° C. for 30 minutes. After being cooled to room temperature, 84.8 mg of 28 wt % sodium methylate/methanol solution was added thereto and the resulting mixture was kept under stirring further for 10 minutes. 50 mL of water was added to the reaction mixture and stirred. The resulting mixture was allowed to stand and then an oil layer was separated. The oil layer was dried over dehydrated sodium sulfate and then sodium sulfate was filtered and concentrated to obtain 99.4 mg of powder of [(R)-N-(5-nitrosalicylidene)-2-amino-1,1-di(2-methoxyphenyl)-1-propanol]copper complex. Yield: 100%.

Example 8

To a 50 mL Schlenk tube purged with nitrogen, 9.94 mg of [(R)-N-(5-nitrosalicylidene)-2-amino-1,1-di(2-methoxyphenyl)-1-propanol]copper complex obtained in Reference Example 1, 3.57 mg of triethoxyaluminum and 5 mL of ethyl acetate were added and stirred at room temperature for 10 minutes to effect reaction and a solution containing optically active copper catalyst composition was obtained. To the solution containing optically active copper catalyst composition, 4 mg of phenylhydrazine was added, and then 7.8 g of 2,5-dimethyl-2,4-hexadiene was added thereto and the resulting mixture was cooled to an inner temperature of 0° C. 5 mL of the ethyl acetate solution containing 1.14 g of ethyl diazoacetate was added dropwise thereto over 2 hours at the same temperature. After adding dropwise, the resulting mixture was stirred at the same temperature for 30 minutes to effect reaction and the reaction mixture containing optically active ethyl 2,2-dimethyl-3-(2-methyl-1-propenyl)cyclopropanecarboxylate was obtained. The yield of optically active ethyl 2,2-dimethyl-3-(2-methyl-1-propenyl)cyclopropanecarboxylate was 86%, and the trans-isomer/cis-isomer ratio=57/43. The residual ratio of ethyl diazoacetate was 0.1%. Optical purity of the trans-isomer was 84% e.e. and that of the cis-isomer was 79% e.e.

Example 9

To a 50 mL Schlenk tube purged with nitrogen, 9.94 mg of [(R)-N-(5-nitrosalicylidene)-2-amino-1,1-di(2-methoxyphenyl)-1-propanol]copper complex obtained in Reference Example 1, 3.57 mg of triethoxyaluminum and 5 mL of ethyl acetate were added and stirred at room temperature for 10 minutes to effect reaction and a solution containing optically active copper catalyst composition was obtained. To the solution containing optically active copper catalyst composition, 4 mg of phenylhydrazine was added, and then 7.8 g of 2,5-dimethyl-2,4-hexadiene was added thereto and the resulting mixture was cooled to an inner temperature of 20° C. 5 mL of the ethyl acetate solution containing 1.41 g of tert-butyl diazoacetate was added dropwise thereto over 2 hours at the same temperature. After adding dropwise, the resulting mixture was stirred at the same temperature for 30 minutes to effect reaction and the reaction mixture containing optically active tert-butyl 2,2-dimethyl-3-(2-methyl-1-propenyl)cyclopropanecarboxylate was obtained. The yield of optically active tert-butyl 2,2-dimethyl-3-(2-methyl-1-propenyl)cyclopropanecarboxylate was 90%, and the trans-isomer/cis-isomer ratio=77/23. The residual ratio of ethyl diazoacetate was 0.1%. Optical purity of the trans-isomer was 91% e.e. and that of the cis-isomer was 62% e.e.

Comparative Example 3

According to the same manner as that described in Example 9, optically active tert-butyl 2,2-dimethyl-3-(2-methyl-1-propenyl)cyclopropanecarboxylate was obtained in a yield of 27% and the trans-isomer/cis-isomer ratio=79/21 except that triethoxyaluminum was not used. The residual ratio of ethyl diazoacetate was 48%. Also, optical purity of the trans-isomer was 91% e.e. and that of the cis-isomer was 62% e.e.

Reference Example 2

In a 200 mL flask, 127 mg of (R)-N-(5-nitrosalicylidene)-2-amino-1,1-di(5-tert-butyl-2-n-butoxyphenyl)-1-propanol, 40 mg of copper(II) acetate monohydrate, and 50 mL of ethyl acetate were added and mixed with stirring at an inner temperature of 50° C. for 30 minutes. After being cooled to room temperature, 84.8 mg of 28 wt % sodium methylate/methanol solution was added thereto and the resulting mixture was kept under stirring further for 10 minutes. 50 mL of water was added to the reaction mixture and stirred. The resulting mixture was allowed to stand and then an oil layer was separated. The oil layer was dried over dehydrated sodium sulfate and then sodium sulfate was filtered and concentrated to obtain 139 mg of powder of [(R)-N-(5-nitrosalicylidene)-2-amino-1,1-di(5-tert-butyl-2-n-butoxyphenyl)-1-propanol]copper complex. Yield: 100%.

Example 10

To a 50 mL Schlenk tube purged with nitrogen, 6.94 mg of [(R)-N-(5-nitrosalicylidene)-2-amino-1,1-di(5-tert-butyl-2-n-butoxyphenyl)-1-propanol]copper complex obtained in Reference Example 2, 1.78 mg of triethoxyaluminum and 5 mL of ethyl acetate were added and stirred at room temperature for 10 minutes to effect reaction and a solution containing optically active copper catalyst composition was obtained. To the solution containing optically active copper catalyst composition obtained, 2 mg of phenylhydrazine was added, and then 7.7 g of 2,5-dimethyl-2,4-hexadiene was added thereto and the resulting mixture was cooled to an inner temperature of 0° C. 5 mL of the ethyl acetate solution containing 1.14 g of ethyl diazoacetate was added dropwise thereto over 2 hours at the same temperature. After adding dropwise, the resulting mixture was stirred at the same temperature for 30 minutes to effect reaction and the reaction mixture containing optically active ethyl 2,2-dimethyl-3-(2-methyl-1-propenyl)cyclopropanecarboxylate was obtained. The yield of optically active ethyl 2,2-dimethyl-3-(2-methyl-1-propenyl)cyclopropanecarboxylate was 83%, and the trans-isomer/cis-isomer ratio=49/51. The residual ratio of ethyl diazoacetate was 0.1%. Optical purity of the trans-isomer was 83% e.e. and that of the cis-isomer was 68% e.e.

Comparative Example 4

According to the same manner as that described in Example 10, optically active ethyl 2,2-dimethyl-3-(2-methyl-1-propenyl)cyclopropanecarboxylate was obtained in a yield of 56% and the trans-isomer/cis-isomer ratio=50/50 except that triethoxyaluminum was not used. The residual ratio of ethyl diazoacetate was 6%. Optical purity of the trans-isomer was 82% e.e. and that of the cis-isomer was 67% e.e.

Reference Example 3

In a 200 mL flask, 89.9 mg of (R)-N-(5-methoxycarbonylsalicylidene)-2-amino-1,1-di(2-methoxyphenyl)-1-propanol, 40 mg of copper(II) acetate monohydrate, and 50 mL of ethyl acetate were added and mixed with stirring at an inner temperature of 50° C. for 30 minutes. After being cooled to room temperature, 84.8 mg of 28 wt % sodium methylate/methanol solution was added thereto and the resulting mixture was kept under stirring further for 10 minutes. 50 mL of water was added to the reaction mixture and stirred. The resulting mixture was allowed to stand and then an oil layer was separated. The oil layer was dried over dehydrated sodium sulfate and then sodium sulfate was filtered and concentrated to obtain 102 mg of powder of [(R)-N-(5-methoxycarbonylsalicylidene)-2-amino-1,1-di(2-methoxyphenyl)-1-propanol]copper complex. Yield: 100%.

Example 11

According to the same manner as that described in Example 10, optically active ethyl 2,2-dimethyl-3-(2-methyl-1-propenyl)cyclopropanecarboxylate was obtained in a yield of 72% and the trans-isomer/cis-isomer ratio=57/43 except that 10.2 mg of [(R)-N-(5-methoxycarbonylsalicylidene)-2-amino-1,1-di(2-methoxyphenyl)-1-propanol] copper complex obtained in Reference Example 3 was used in place of 6.94 mg of [(R)-N-(5-nitrosalicylidene)-2-amino-1,1-di(5-tert-butyl-2-n-butoxyphenyl)-1-propanol]copper complex obtained in Reference Example 2. The residual ratio of ethyl diazoacetate was 11%. Optical purity of the trans-isomer was 85% e.e. and that of the cis-isomer was 80% e.e.

Comparative Example 5

According to the same manner as that described in Example 11, optically active ethyl 2,2-dimethyl-3-(2-methyl-1-propenyl)cyclopropanecarboxylate was obtained in a yield of 35% and the trans-isomer/cis-isomer ratio=58/42 except that triethoxyaluminum was not used. The residual ratio of ethyl diazoacetate was 45%. Optical purity of the trans-isomer was 84% e.e. and that of the cis-isomer was 79% e.e.

Reference Example 4

According to the same manner as that described in Reference Example 3, 95.6 mg of powder of [(R)-N-(5-cyanosalicylidene)-2-amino-1,1-di(2-methoxyphenyl)-1-propanol]copper complex was obtained except that 83.3 mg of (R)-N-(5-cyanosalicylidene)-2-amino-1,1-di(2-methoxyphenyl)-1-propanol was used in place of 89.9 mg of (R)-N-(5-methoxycarbonylsalicylidene)-2-amino-1,1-di(2-methoxyphenyl)-1-propanol. Yield: 100%.

Example 12

According to the same manner as that described in Example 10, optically active ethyl 2,2-dimethyl-3-(2-methyl-1-propenyl)cyclopropanecarboxylate was obtained in a yield of 52% and the trans-isomer/cis-isomer ratio=57/43 except that 9.56 mg of [(R)-N-(5-cyanosalicylidene)-2-amino-1,1-di(2-methoxyphenyl)-1-propanol]copper complex obtained in Reference Example 4 was used in place of 6.94 mg of [(R)-N-(5-nitrosalicylidene)-2-amino-1,1-di(5-tert-butyl-2-n-butoxyphenyl)-1-propanol]copper complex obtained in Reference Example 2. The residual ratio of ethyl diazoacetate was 26%. Optical purity of the trans-isomer was 85% e.e. and that of the cis-isomer was 80% e.e.

Comparative Example 6

According to the same manner as that described in Example 12, optically active ethyl 2,2-dimethyl-3-(2-methyl-1-propenyl)cyclopropanecarboxylate was obtained in a yield of 29% and the trans-isomer/cis-isomer ratio=58/42 except that triethoxyaluminum was not used. The residual ratio of ethyl diazoacetate was 59%. Optical purity of the trans-isomer was 84% e.e. and that of the cis-isomer was 79% e.e.

Comparative Example 7

According to the same manner as that described in Example 10, optically active ethyl 2,2-dimethyl-3-(2-methyl-1-propenyl)cyclopropanecarboxylate was obtained in a yield of 6% and the trans-isomer/cis-isomer ratio=59/41 except that 22.65 mg of [(R)-N-salicylidene-2-amino-1,1-di(2-methoxyphenyl)-1-propanol]copper complex was used in place of 6.94 mg of [(R)-N-(5-nitrosalicylidene)-2-amino-1,1-di(5-tert-butyl-2-n-butoxyphenyl)-1-propanol]copper complex obtained in Reference Example 2. The yield of dimerization by-product was 6% and the residual ratio of ethyl diazoacetate was 84%. Optical purity of the trans-isomer was 50% e.e. and that of the cis-isomer was 49% e.e.

Comparative Example 8

According to the same manner as that described in Comparative Example 7, optically active ethyl 2,2-dimethyl-3-(2-methyl-1-propenyl)cyclopropanecarboxylate was obtained in a yield of 5% and the trans-isomer/cis-isomer ratio=59/41 except that triethoxyaluminum was not used. The yield of dimerization by-product was 10% and the residual ratio of ethyl diazoacetate was 84%. Optical purity of the trans-isomer was 48% e.e. and that of the cis-isomer was 47% e.e.

Example 13

According to the same manner as that described in Example 8, optically active ethyl 2,2-dimethyl-3-(2-methyl-1-propenyl)cyclopropanecarboxylate was obtained in a yield of 85% and the trans-isomer/cis-isomer ratio=57/43 except that 0.84 mg of lithium methoxide was used in place of 3.57 mg of triethoxyaluminum. The residual ratio of ethyl diazoacetate was 0.1%. Optical purity of the trans-isomer was 85% e.e. and that of the cis-isomer was 78% e.e.

Example 14

According to the same manner as that described in Example 8, optically active ethyl 2,2-dimethyl-3-(2-methyl-1-propenyl)cyclopropanecarboxylate was obtained in a yield of 86% and the trans-isomer/cis-isomer ratio=58/42 except that 0.53 mg of lithium hydroxide was used in place of 3.57 mg of triethoxyaluminum. The residual ratio of ethyl diazoacetate was 0.1%. Optical purity of the trans-isomer was 81% e.e. and that of the cis-isomer was 75% e.e.

Example 15

According to the same manner as that described in Example 8, optically active ethyl 2,2-dimethyl-3-(2-methyl-1-propenyl)cyclopropanecarboxylate was obtained in a yield of 82% and the trans-isomer/cis-isomer ratio=58/42 except that 0.57 mg of lithium fluoride was used in place of 3.57 mg of triethoxyaluminum. The residual ratio of ethyl diazoacetate was 0.1%. Optical purity of the trans-isomer was 81% e.e. and that of the cis-isomer was 76% e.e.

INDUSTRIAL APPLICABILITY

According to the present invention, diazotization reaction catalyst which exhibits good activity can be obtained. The catalyst exhibits good activity, for example, at low reaction temperature. It is possible to produce an optically active cyclopropane compound easily by using the catalyst.

The invention claimed is:

1. An optically active copper catalyst composition comprising
   (a) an optically active salicylideneaminoalcohol represented by the formula (1):

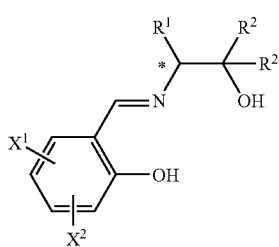

wherein $R^1$ and $R^2$ are the same or different, and independently represent a substituted or unsubstituted lower alkyl group, a substituted or unsubstituted aralkyl group, or a substituted or unsubstituted aryl group;
   $X^1$ and $X^2$ are the same or different, and independently represent a hydrogen atom, a lower alkoxy group, a nitro group, a lower alkoxycarbonyl group, a cyano group or a halogen atom; and * represents an asymmetric center, provided that both of $X^1$ and $X^2$ don't represent hydrogen atoms,
   (b) a monovalent or divalent copper compound, and
   (c-1) a lithium compound or
   (c-2) a compound selected from aluminum compounds having Lewis acidity, titanium compounds having Lewis acidity, boron compounds having Lewis acidity, zirconium compounds having Lewis acidity and hafnium compounds having Lewis acidity.

2. An organic solvent solution or a slurry containing the optically active copper catalyst composition according to claim 1, which is obtained by contacting the optically active salicylideneaminoalcohol represented by the formula (1), the monovalent or divalent copper compound, and the lithium compound or the compound selected from c-2) in an organic solvent.

3. The optically active copper catalyst composition according to claim 1, or the organic solvent solution or the slurry containing the composition according to claim 2, which is obtained by contacting the optically active salicylideneaminoalcohol represented by the formula (1), the monovalent or divalent copper compound, and the lithium compound.

4. The optically active copper catalyst composition according to claim 1, or the organic solvent solution or the slurry containing the composition according to claim 2, which is obtained by contacting the optically active salicylideneaminoalcohol represented by the formula (1), the monovalent or divalent copper compound, and the Lewis acid.

5. The optically active copper catalyst composition according to claim 1, wherein the lithium compound is lithium salt, lithium alkoxide or lithium hydroxide.

6. The optically active copper catalyst composition according to claim 1, wherein aluminum compounds having Lewis acidity is trihaloaluminum, trialkylaluminum, trialkoxyaluminum, triaryloxyaluminum, or tris(pentafluorophenyl)aluminum, titanium compounds having Lewis acidity is tetrahalotitanium or tetraalkoxytitanium, boron compounds having Lewis acidity is boron trifluoride diethyl etherate, triethylborane, triphenylborane, or tris(pentafluorophenyl)borane, zirconium compounds having Lewis acidity is zirconium halide (IV) or the complex, or tetraalkoxyzirconium, and hafnium compounds having Lewis acidity is hafnium halide (IV) or the complex.

7. The optically active copper catalyst composition according to claim 6, wherein aluminum compounds having Lewis acidity is trimethylaluminum, triethylaluminum, triisobutylaluminum, triethoxyaluminum, or triphenoxyaluminum, titanium compounds having Lewis acidity is titanium tetrahalide, tetraisopropoxytitanium or tetra(n-butoxy)titanium, zirconium compounds having Lewis acidity is zirconium tetrachloride, zirconium tetrachloride tetrahydrofuran complex or tetra(n-butoxy)zirconium, and hafnium compounds having Lewis acidity is hafnium tetrachloride or hafnium tetrachloride tetrahydrofuran complex.

8. The optically active copper catalyst composition according to claim 1 or the organic solvent solution or the slurry containing the composition according to claim 2, wherein the compound selected from (c-2) is methoxylithium, triethoxyaluminum, tris(pentafluorophenyl)aluminum, tetraisopropoxytitanium or tris(pentafluorophenyl)borane.

9. The optically active catalyst complex composition according to claim 1, wherein the amount of the compound selected from (c-2) used is 0.3 to 5 moles per 1 mole of the monovalent or divalent copper compound.

10. The organic solvent solution or the slurry containing the optically active copper catalyst composition according to claim 2, wherein the amount of the compound selected from (c-2) used is 0.3 to 5 moles per 1 mole of the monovalent or divalent copper compound.

11. The optically active copper catalyst composition according to claim 1, or the organic solvent solution or the slurry containing the composition according to claim 2, wherein the monovalent or divalent copper compound is a C2-5 copper organic carboxylate, copper halide, copper methanesulfonate, copper trifluoromethanesulfonate, copper carbonate or copper hydroxide.

12. A process for producing an optically active cyclopropane compound represented by the formula (4):

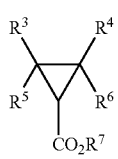

wherein $R^3$, $R^4$, $R^5$ and $R^6$ are the same or different, and independently represent a hydrogen atom, an alkyl group which may be substituted with one or more halogen atom, an alkenyl group which may be substituted with one or more halogen atom, an aryl group or an aralkyl group; provided that, when $R^3$ and $R^5$ are the same, $R^3$ and $R^4$ are different from each other; and $R^7$ represents a C1–6 alkyl group, which comprises reacting a prochiral olefin represented by the formula (2):

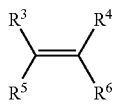 (2)

wherein $R^3$, $R^4$, $R^5$ and $R^6$ are as defined above, with a diazoacetic acid ester represented by the formula (3):

$$N_2CHCO_2R^7 \qquad (3)$$

wherein $R^7$ is as described above, in the presence of the optically active copper catalyst composition according to claim 1, or the organic solvent solution or the slurry containing the composition according to claim 2.

13. The process for producing an optically active cyclopropane compound according to claim 12, wherein the prochiral olefin (2) is 2,5-dimethyl-2,4-hexadiene.

* * * * *